US006285904B1

United States Patent
Weber et al.

(10) Patent No.: US 6,285,904 B1
(45) Date of Patent: Sep. 4, 2001

(54) METHOD AND APPARATUS FOR DETERMINING FAT CONTENT OF TISSUE

(75) Inventors: Thomas M. Weber; Barry L. Spletzer, both of Albuquerque; Jon R. Bryan, Edgewood; Fred M. Dickey; Richard N. Shagam, both of Albuquerque, all of NM (US); Luc Gooris, Rancho Santa Margarita, CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/536,280

(22) Filed: Mar. 27, 2000

(51) Int. Cl.[7] .......................................................... A61B 6/00
(52) U.S. Cl. ............................................ 600/473; 600/476
(58) Field of Search ................................... 600/407, 473, 600/476

(56) References Cited

U.S. PATENT DOCUMENTS

| 5,014,713 | | 5/1991 | Roper et al. . |
| 5,492,118 | * | 2/1996 | Gratton et al. . |
| 5,497,769 | * | 3/1996 | Gratton et al. . |
| 5,752,519 | * | 5/1998 | Benaron et al. . |
| 6,032,064 | * | 2/2000 | Devlin et al. . |
| 6,078,833 | * | 6/2000 | Hueber . |
| 6,208,887 | * | 3/2001 | Clarke . |

OTHER PUBLICATIONS

Conway, et al, "A New Approach for the Estimation of Body Composition: Infrared Interactance,[1,2]" The American Journal of Clinical Nutrition 40: Dec. 1984, pp 1123–1130.

Cui; Ostrander, "The Relationship of Surface Reflectance Measurements to Optical Properties of Layered Biological Media, " IEEE Transactions of Biomedical Engineering, vol. 39, No. 2, Feb. 1992.

Lanza, Determination of Moisture, Proetin, Fat and Calories in Raw Pork and Beef by Near Infrared Spectroscopy, Journal of Food Science, vol. 48, pp 471–473, 1983.

Microchip Technology PIC168F87X Datasheet, Dec. 1999.

Burr–Brown, LOG 100 Datasheet, Jan. 1995.

* cited by examiner

*Primary Examiner*—Marvin M. Lateef
*Assistant Examiner*—Runa Shah Qaderi
(74) *Attorney, Agent, or Firm*—V. Gerald Grafe

(57) ABSTRACT

A method and apparatus for determining characteristics of tissue is disclosed. The method comprises supplying optical energy to a tissue and detecting at a plurality of locations consequent energy scattered by the tissue. Analysis of the scattered energy as taught herein provides information concerning the properties of the tissue, specifically information related to the fat and lean content and thickness of the tissue. The apparatus comprises a light source adapted to deliver optical energy to a tissue. A plurality of detectors can be mounted at different positions relative to the source to detect energy scattered by the tissue. A signal processor as taught herein can determine characteristics of the tissue from the signals from the detectors and locations of the detectors, specifically information related to the fat and lean content and thickness of the tissue.

11 Claims, 2 Drawing Sheets

METHOD AND APPARATUS FOR DETERMINING FAT CONTENT OF TISSUE

This invention was made with Government support under Contract DE-AC04-94AL85000 awarded by the U.S. Department of Energy. The Government has certain rights in the invention.

BACKGROUND OF THE INVENTION

This invention relates to the field of determining properties of tissue, specifically characterizing meat as to fat and lean content and thickness.

Automated trimming of fat from meat is difficult without a sensor capable of accurately indicating the thickness of a fat layer to be trimmed. Automated detection of unsuitable fat content of meat products similarly requires a sensor capable of accurately indicating the fat content of the meat. Existing sensors are inadequate. See, e.g., Roper, U.S. Pat. No. 5,014,713.

SUMMARY OF THE INVENTION

The present invention provides a method and apparatus for determining characteristics of tissue. The method comprises supplying optical energy to a tissue and detecting at a plurality of locations consequent energy scattered by the tissue. Analysis of the scattered energy as taught herein can provide information concerning the properties of the tissue, specifically information related to the fat and lean content of the tissue.

A sensor according to the present invention comprises a light source adapted to deliver optical energy to a tissue. A plurality of detectors can be mounted at different positions relative to the source to detect energy scattered by the tissue. A signal processor as taught herein can determine characteristics of the tissue from the signals from the detectors and locations of the detectors.

Advantages and novel features will become apparent to those skilled in the art upon examination of the following description or may be learned by practice of the invention. The objects and advantages of the invention may be realized and attained by means of the instrumentalities and combinations particularly pointed out in the appended claims.

DESCRIPTION OF THE FIGURES

The accompanying drawings, which are incorporated into and form part of the specification, illustrate embodiments of the invention and, together with the description, serve to explain the principles of the invention.

DETAILED DESCRIPTION OF THE INVENTION

The present invention provides a sensor that can indicate the characteristics of tissue, e.g., fat content (presence or proportion of fat) and layer thickness (thickness of a layer of fat above lean tissue).

Figure 1:
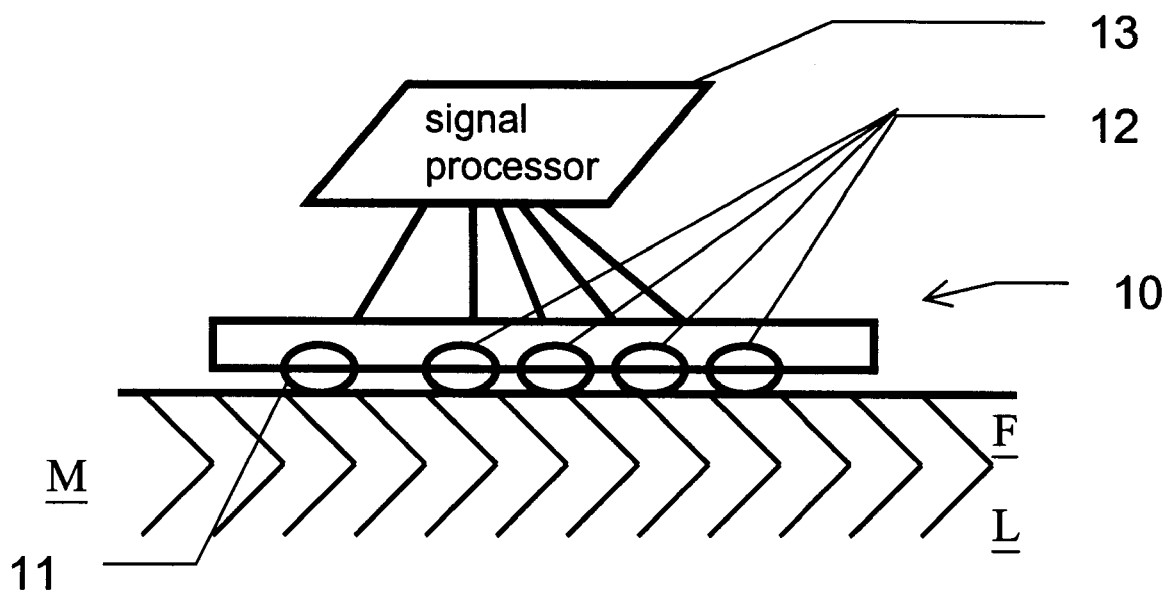
FIG. 1 is a schematic representation of a sensor according to the present invention.

FIG. 1 is a schematic representation of a sensor 10 according to the present invention. Sensor 10 comprises a light source 11 and a plurality of detectors 12 mounted at different radial distances from light source 11. Sensor 10 further comprises a signal processor 13 receiving signals indicative of detected light intensity from detectors 12.

Light source 11 can be an infrared or red LED, for example the HP HSDL-4400 or IF-E97. See Hewlett Packard HSDL-44xx datasheet, incorporated herein by reference; Industrial Fiber Optics IF-E97 datasheet, incorporated herein by reference. Detectors 12 can be any light sensitive detector, for example a plurality of discrete detectors such as IF-D91 photodiodes or HSDL-5400 detectors, or a CCD array such as the TSL215. See Industrial Fiber Optics IF-D91 datasheet, incorporated herein by reference; Hewlett Packard HSDL-54xx datasheet, incorporated herein by reference; Texas Instruments TSL215 datasheet, incorporated herein by reference. Signal processor 13 can be electronic circuitry designed to accomplish the desired processing of the detector outputs and distances, or can be a general purpose computer programmed to accomplish the desired processing of the detector outputs and distances.

In operation, sensor 10 is placed proximal to tissue T so that light source 11 and detectors 12 are near or in contact with tissue T. Placing the light source or the detectors in contact with tissue T can reduce surface reflections to the detectors, simplifying the rest of the system. Light from light source 11 enters and is scattered by tissue T. Some of the scattered light reaches the detectors 12, as shown in FIG. 1b. Fat F and lean L portions of tissue T have different light scattering properties, and so the pattern of scattered light reaching detectors 12 varies with varying thickness of fat F.

Figure 2:
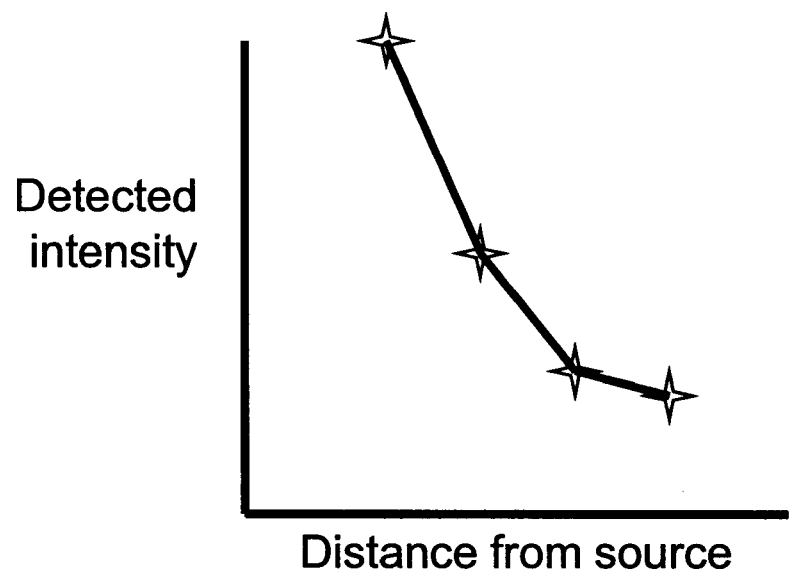
FIG. 2 is a graph of representative detector signals.

Signal processor 13 receives signals indicative of the light received by each detector 12. Those signals, combined with specification of the radial distance to each detector, allows the signal processor to indicate the characteristics of the tissue. For example, the rate of change of scattered light intensity (the slope of the curve in FIG. 2) can indicate fat content since fat and lean tissue scattering leads to different slopes. As another example, the total area under the curve can indicate fat thickness since different fat thicknesses lead to different total light scattered.

Linear regression techniques known to those skilled in the art can produce a slope of about −15 for lean meat or membrane, and a slope of about −45 for fat. The slope accordingly is indicative of fat content of the tissue.

A mask, partially shielding detectors 12 from scattered light can also be used in the present invention. For example, a mask that completely blocks scattered light from the region closest to the light source can prevent saturation of the closest detectors and accompanying measurement errors. As another example, a mask that shields detectors 12 according to radial distance (greatest shielding at closest radial distance) can compensate for dynamic range limitations of detectors by blocking known proportions of scattered light in regions where the scattered light intensity is greatest. As another example, a mask that shields detectors according to radial distance can be used to correct for the different areas represented by different radial distances (since the area corresponding to distant detectors is greater than the area corresponding to near detectors). Suitable masks can be produced by printing a varying gray scale density onto plastic film using a laser printer, for example.

Another means of increasing the dynamic range of the sensor is to use pulses of optical energy at different power levels. At a lower power level, only those detectors near the source are integrated, and at a higher power level, only those detectors farther away from the source are integrated. The results from the low and high power optical pulses can be combined to obtain the total response. This technique prevents saturation of the detectors near the source and ensures that the full dynamic range of the detectors far from the source is utilized. Using this technique can eliminate the need for a mask or filter in front of the detectors.

EXAMPLE CCD IMPLEMENTATION

Figure 3:
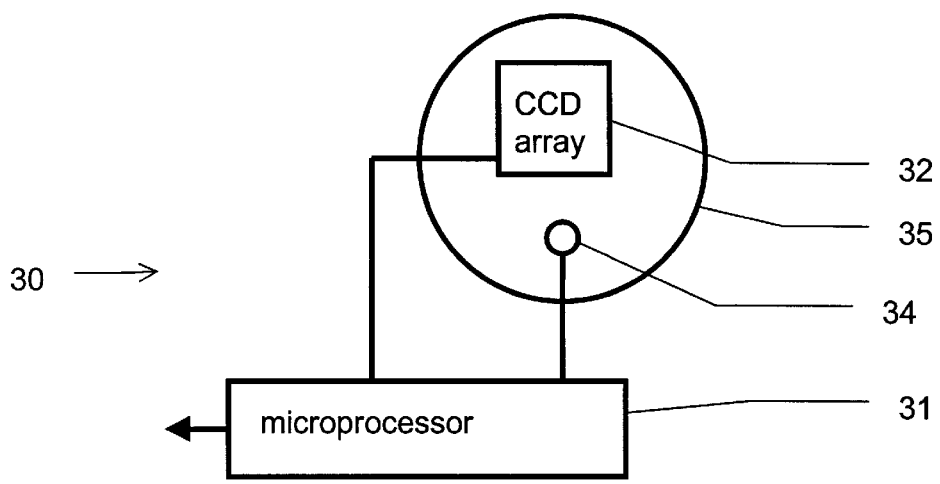
FIG. 3 is a schematic representation of a sensor according to the present invention.

FIG. 3 is a schematic representation of a sensor 30 according to the present invention. Infrared light source 34 and CCD array 32 mount with sensor housing 35. Infrared light source 34 can be an infrared light emitting diode, such as the HSDL-4400, for example. CCD array 32 can be a commercially available CCD array such as the TSL215. Infrared light source 34 can be mounted to maintain a separation from CCD array 32 so that transmission of light from infrared light source 34 directly to CCD array 32 is discouraged. A separation of about 0.15 inch can be suitable. Infrared light source 34 and CCD array 32 can further be potted, for example by filling the surrounding volume with black epoxy, to further discourage direct light transmission and reduce errors due to ambient light.

A microprocessor 31 can be connected to detect outputs of CCD array 32 and to control infrared light source 34. A microprocessor such as a PIC16F876 can be suitable. See Microchip Technology PIC168F87X datasheet, incorporated herein by reference. LED driver 32 can be controlled by microprocessor 31 to energize infrared light source 34. Microprocessor 31 can also comprise software suitable for analyzing the outputs of the CCD array and outputting an indication of fat thickness. An example of suitable pseudocode is shown in Table 1.

TABLE 1

| | |
|---|---|
| CCD.trigger | % signal CCD array to output an array of readings |
| dark[j] = CDD[j] | % store CDD values with no illumination |
| LED.on | % turn on LED |
| CCD.latch | % signal CCD array to latch a reading |
| detected[j] = CCD[j] | % store CCD values while illuminated |
| LED.off | % turn off LED |
| illuminated[j] = detected[j] − dark[j] | % subtract base values from detected values |
| fat.content(illuminated[j],position[j]) | % determine fat content from slope or integral of illuminated[j] |

EXAMPLE TWO DETECTOR IMPLEMENTATION

Figure 4:
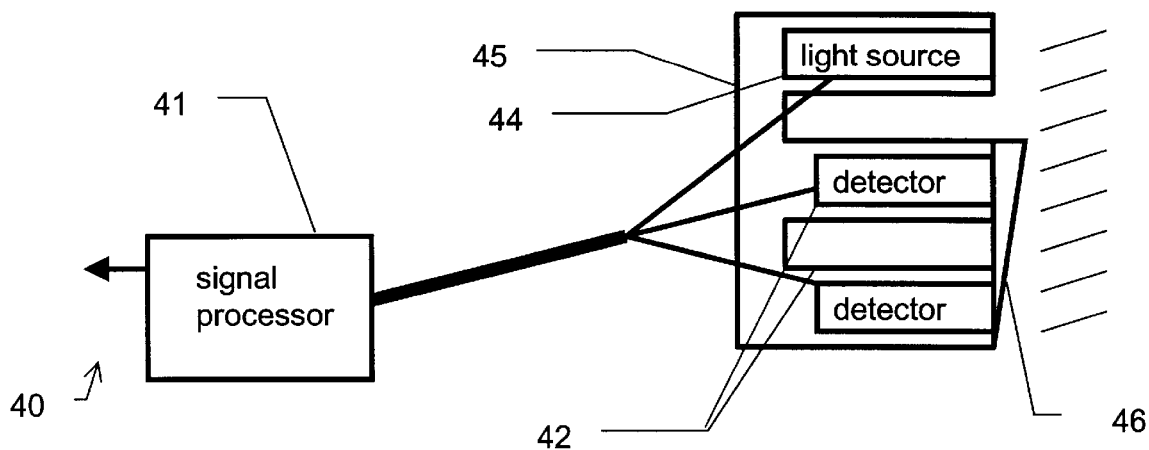
FIG. 4 is a schematic representation of a sensor according to the present invention.

FIG. 4 is a schematic representation of a sensor according to the present invention. Light source 44 and two detectors 42 mount at defined distances from each other, for example with tines of a fork. Light source 44 can be, for example, an infrared light emitting diode such as the HSDL-4400 or IF-E97. Detectors 42 can be, for example, the HSDL-5400 or the IF-D91. Light source and detectors can mount directly with housing 45, or can mount remotely and be optically coupled with housing 45 with optical fibers. Detectors 42 mounted 0.1 inch and 0.25 inch from light source 44 can be suitable. A mask 46 can mount between detectors 42 and tissue to be investigated, providing some dynamic range compensation. Light source 44 and detectors 42 can are connected to and controlled by signal processor 41. Signal processor 41 controls the energization of light source 42, and determines fat content from the outputs of detectors 44. For example, a Log1100 log amplifier commercially available from Burr-Brown can combine the detector outputs and generate an indication of fat content based on the slope of the response across the distance between the two detectors. See Burr-Brown Log100 datasheet, incorporated herein by reference.

EXAMPLE SIGNAL PROCESSOR IMPLEMENTATION

A signal processor suitable for use in the present invention can be built using circuit design and programming techniques known to those skilled in the art, based on the functions described above. The signal processor must have input/output resources and corresponding hardware or software capabilities suitable for controlling the operation of the light source and detectors according to the functions described above. It must also have hardware or software capabilities suitable for performing the analysis described above and outputting the results in a format suitable to the intended application.

The particular sizes and equipment discussed above are cited merely to illustrate particular embodiments of the invention. It is contemplated that the use of the invention may involve components having different sizes and characteristics. It is intended that the scope of the invention be defined by the claims appended hereto.

We claim:

1. A tissue characterization sensor, comprising:
   a) a housing;
   b) a source of optical energy mounted with the housing, disposed so as to deliver optical energy to tissue;
   c) a plurality of detectors mounted with the housing at different locations, within a range of locations, relative to the source, disposed so as to detect energy scattered by the tissue in response to delivered optical energy;
   d) a signal processor adapted to indicate fat thickness from the energy detected by each detector and the location of each detector relative to the location of the source of optical energy;
   e) wherein the plurality of detectors comprises a mask mounted with the detectors and reducing the optical energy reaching each detector by an proportion increasing with increasing radial distance of each detector to the source.

2. The sensor of claim 1, wherein the plurality of detectors are mounted at different radial distances relative to the source.

3. The sensor of claim 1, wherein the housing is configured to maintain the source in contact with the tissue.

4. The sensor of claim 3, wherein the housing comprises a fork having three tines, with the source mounted with a first tine, and detectors mounted with second and third tines.

5. The sensor of claim 1, wherein the housing is configured to maintain the detectors in contact with the tissue.

6. The sensor of claim 5, wherein the housing comprises a fork having three tines, with the source mounted with a first tine, and detectors mounted with second and third tines.

7. The sensor of claim 1, wherein the plurality of detectors comprises a first detector mounted at a first radial distance from the source, and a second detector mounted at a second radial distance from the source.

8. The sensor of claim 1, wherein the plurality of detectors comprises a CCD array.

9. The sensor of claim 1, wherein the source of optical energy comprises a source capable of delivering optical energy at a plurality of power levels.

10. The sensor of claim 1, wherein the signal processor is configured to determine the rate of change of detected energy with respect to detector location.

11. The sensor of claim 1, wherein the signal processor is configured to integrate the energy detected over the range of detector locations.

* * * * *